US012793859B2

United States Patent
(12) United States Patent
Jayaraman et al.

(10) Patent No.: US 12,793,859 B2
(45) Date of Patent: Nov. 10, 2026

(54) METHOD AND SYSTEM FOR ANALYZING CARDIAC ACTIVITY BY MODELLING CARDIAC M-CELLS

(71) Applicant: Tata Consultancy Services Limited, Mumbai (IN)

(72) Inventors: Srinivasan Jayaraman, Edison, NJ (US); Ponnuraj Kirthi Priya, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1215 days.

(21) Appl. No.: 17/741,630

(22) Filed: May 11, 2022

(65) Prior Publication Data

US 2022/0406468 A1 Dec. 22, 2022

(30) Foreign Application Priority Data

May 14, 2021 (IN) ............................ 202121021835

(51) Int. Cl.
*G16H 50/50* (2018.01)
*A61B 5/00* (2006.01)

(52) U.S. Cl.
CPC .......... *G16H 50/50* (2018.01); *A61B 5/7278* (2013.01)

(58) Field of Classification Search
CPC ............................. G16H 50/50; A61B 5/7278
See application file for complete search history.

(56) References Cited

U.S. PATENT DOCUMENTS

2009/0048815 A1 2/2009 Hamm et al.

FOREIGN PATENT DOCUMENTS

CN 102086484 B 5/2016

OTHER PUBLICATIONS

Ponnuraj Kirthi Priya and M. Ramasubba Reddy, (2017), Study of factors affecting the progression and termination of drug induced Torsade de pointes in two dimensional cardiac tissue, Journal of Electrocardiology, vol. 50, Issue 3, pp. 332-341. DOI: 10.1016/j.jelectrocard.2017.01.016.*

(Continued)

*Primary Examiner* — Karlheinz R. Skowronek
*Assistant Examiner* — Blake H. Elkins
(74) *Attorney, Agent, or Firm* — Finnegan, Henderson, Farabow, Garrett & Dunner, LLP

(57) ABSTRACT

The ventricular myocardium in the heart is composed of three cell layer: endocardial, mid-myocardial and epicardial cells. A specific group of myocardial cells termed as M-cells exists in the deep sub-endocardium and mid-myocardium that have a longer action potential duration in comparison to other cell types. A method and system have been provided for analyzing cardiac activity by modelling myocardial cells (M-cells). The method comprises preparing a computational tool that will allow biologists to analyze and retrieve cardiac cellular information automatically and enable discovering of relationships between cellular and cardiovascular system utilizing the M-cells. The method is configured to understand how the properties of M-cells affect the generation of T-wave and how they contribute to arrhythmogenesis in short QT syndrome 2. Pseudo ECGs is created by exciting the tissue in order to analyze the morphology of the T-wave.

16 Claims, 11 Drawing Sheets

(56) References Cited

OTHER PUBLICATIONS

Cunjin Luo, Kuanquan Wang, and Henggui Zhang, (2016), Functional Effects of Island-Distribution of Mid-cardiomyocytes on Re-entrant Excitation Waves in the KCNQ1-linked Short QT Syndrom, Computing in Cardiology, vol. 43, pp. 1-4. DOI: 10.22489/CinC.2016.271-177.*
Ponnuraj Kirthi Priya and M. Ramasubba Reddy, (2017), Effect of Regional Cellular Uncoupling in presence of LQTS2 in a 2D Cardiac Tissue, 2017 IEEE 17th International Conference on Bioinformatics and Bioengineering, pp. 383-387. DOI: 10.1109/BIBE.2017.00071.*
M. Mhajna and S. Abboud (2013), Assessment of cardiac stroke volume in patients with implanted cardiac pacemaker using parametric electrical impedance tomography: A theoretical 2D study, International Journal for Numerical Methods in Biomedical Engineering, vol. 29: 630-640. DOI: 10.1002/cnm.2550. (Year: 2013).*
Howard S. Oster, Bruno Taccardi, Robert L. Lux, et al. (1998), Electrocardiogramaging: Noninvasive Characterization of Intramural Myocardial Activation From Inverse-Reconstructed Epicardial Potentials and Electrograms, Circulation, vol. 97, No. 15: 1496-1507. DOI: 10.1161/01.CIR.97.15.1496. (Year: 1998).*
Ponnuraj K. Priya and Srinivasan Jayaraman (2020), Do M-cells contribute significantly in T-wave morphology during normal and arrhythmogenesis conditions like short QT Syndrome?, biorxiv: 1-23. DOI: 10.1101/2020.05.28.121079. (Year: 2020).*
Ponnuraj K. Priya and M. Ramasubba Reddy (2017), Simulation study of the ionic mechanisms underlying Torsade de Pointes in a 2D cardiac tissue, Computers in Biology and Medicine, vol. 89: 293-303. DOI: 10.1016/j.compbiomed.2017.08.017. (Year: 2017).*
Diniş et al., "Modeling and Simulation of Processes from an Iron Ore Sintering Plant," (2008).
Tiebin et al., "Quality prediction modeling for sintered ores based on mechanism models of sintering and extreme learning machine based error compensation," E3S Web of Conferences, 38 (2018).

* cited by examiner

METHOD AND SYSTEM FOR ANALYZING CARDIAC ACTIVITY BY MODELLING CARDIAC M-CELLS

PRIORITY CLAIM

This U.S. patent application claims priority under 35 U.S.C. § 119 to: Indian Patent Application No. 202121021835, filed on 14 May 2021. The entire contents of the aforementioned application are incorporated herein by reference.

TECHNICAL FIELD

The disclosure herein generally relates to the field of analyzing cardiac health, and, more particularly, to a system and method for analyzing cardiac activity by modelling myocardial cells (M-cells) in the heart.

BACKGROUND

A Human body is a complex system which incorporates several sub systems that efficiently interact with each other to run the body. It is important to understand the physiology of the human body. An accurate understanding of the human body leads to development of a medical device or a drug. In a total product life cycle of a medical device or a drug, reducing the burden of enrolling real patients in the clinical trial is critical for mankind. Moreover, focus should be patient centric rather than disease centric.

Physiological modelling is one of the ways to understand physiology, which aims to understand the individual role of each part at various multi-scales (molecules to organ) that contribute to the functioning of the integrated whole body. This is carried out by characterizing the distinct biological process at a particular scale level using data obtained from experiments.

Among various physiological systems, the heart has been extensively modelled. A first successful model, demonstrated the action potential generated in neuron with relation to underlying ion channel conduction and gating dynamics. Computational models of cardiac cells and tissue electrophysiology are being used to quantitatively describe action potential propagation.

The ventricular myocardium in the heart is composed of three cell layers: endocardial (endo), mid-myocardial (mid) and epicardial (epi) cells that vary in their action potential (AP) shape and duration due to the intrinsic differences in their electrophysiological properties. In addition, a specific group of myocardial cells termed as M-cells exist in the deep sub-endocardium and mid-myocardium that have a longer action potential duration in comparison to other cell types. These cells are a major contributor to the existence of transmural dispersion of repolarization (TDR). In an intact myocardium, it is observed that the action potential depolarization (APD) increases from the epicardium to the mid-myocardium reaching a maximum value in the deeper layers and then reducing at the endocardium.

The M-cells account for 30-40% of the ventricular wall and this relative abundance plays an important role in a number of electrophysiological phenomena including U-waves and biphasic T-waves. During disease conditions, the mean APD increases and the maximum APD gradient increases markedly. Selective prolongation of APD of M-cells has been known to act as a substrate for promoting conduction block and re-entrant arrhythmia. The morphology of the T-wave has been attributed to the differences in the repolarization times of these different cell types that inherently exist in the ventricular wall as well as the degree of electro-tonic coupling. An amplification of this dispersion of repolarization (DOR) due to genetic factors or effect of drugs has been known to contribute to the development of various cardiac arrhythmia. These issues emphasize to better understand the functional characteristics of M-cells in both normal and diseased conditions.

SUMMARY

Embodiments of the present disclosure present technological improvements as solutions to one or more of the above-mentioned technical problems recognized by the inventors in conventional systems. For example, in one embodiment, a system for analyzing cardiac activity by modelling the cardiac cells with myocardial cells (M-cells) is provided. The system comprises an input/output interface, one or more hardware processors and a memory. The memory is in communication with the one or more hardware processors, wherein the one or more first hardware processors are configured to execute programmed instructions stored in the one or more first memories, to: generate a cell model including the M-cells present in mid-myocardium of heart, wherein the cell model is configured to simulate the performance of rise and fall of action potential of the cardiac cell using a differential equation; generate processors, a tissue model of a transmural section of one or more of a 2D ventricular tissue or a 3D ventricular tissue of the heart using the cell model, wherein the 2D ventricular tissue is made of an array of cells interconnected by gap junction conductance (GJC); model a functionality of the gap junction conductance that allows passage of electric current between the M-cells using a plurality of conductive elements; simulate a plurality of properties of the M-cells, if all the cells in the mid-myocardium are considered to be M-cells, wherein the simulation includes a fivefold decrease in the GJC at an epi-mid mural junction along the whole length of the mid-myocardium, whereas there is no reduction in the GJC at the endo-mid interface; simulate a plurality of properties of a plurality of M-cell islands, if each M-cell island is considered to be either located completely within the mid myocardium or partially in the endocardium layer; record the effect of physical characteristics of the M-cells on arrhythmogenesis by altering a position, a shape and a size of the M-cells in a plurality of configurations using the simulated M-cells and the plurality of properties of M-cell islands; synthesize a pseudo-ECG by exciting the tissues present in the tissue model, wherein the M-cells present in the tissue model get excited and stimulate neighboring cells by creating a convex wave-front travelling from the endocardium to epicardium and from an apex to a base of the heart; and realize the effect of short QT syndrome in the tissue model by changing a rectifying potassium current of M-cells to detect cardiac abnormality In another aspect, a method for analyzing cardiac activity by modelling the cardiac cells with myocardial cells (M-cells) is provided. Initially, a cell model including the M-cells present in mid-myocardium of heart is generated, wherein the cell model is configured to simulate the performance of rise and fall of action potential of the cardiac cell using a differential equation. Further, a tissue model of a transmural section of one or more of a 2D ventricular tissue or a 3D ventricular tissue of the heart is generated using the cell model, wherein the 2D ventricular tissue is made of an array of cells interconnected by gap junction conductance (GJC). In the next step, a functionality of the gap junction conductance that allows passage of electric current between the M-cells using a plurality of conductive elements is modelled. In the next step, a plurality of properties of the M-cells is simulated, if all the cells in the mid-myocardium are considered to be M-cells, wherein the simulation includes a fivefold decrease in the GJC at an epi-mid mural junction along the whole length of the mid-myocardium, whereas there is no reduction in the GJC at the endo-mid interface. Similarly, a plurality of properties of a plurality of M-cell islands is also simulated, if each M-cell island is considered to be either located completely within the mid myocardium or partially in the endocardium layer. In the next step, the effect of physical characteristics of the M-cells is recorded on arrhythmogenesis by altering a position, a shape and a size of the M-cells in a plurality of configurations using the simulated M-cells and the plurality of properties of M-cell islands. Further, a pseudo-ECG is synthesized by exciting the tissues present in the tissue model, wherein the M-cells present in the tissue model get excited and stimulate neighboring cells by creating a convex wave-front travelling from the endocardium to epicardium and from an apex to a base of the heart. And finally, the effect of short QT syndrome is realized in the tissue model by changing a rectifying potassium current of M-cells to detect cardiac abnormality.

In yet another aspect, one or more non-transitory machine readable information storage mediums comprising one or more instructions which when executed by one or more hardware processors cause analyzing cardiac activity by modelling the cardiac cells with myocardial cells (M-cells) is provided. Initially, a cell model including the M-cells present in mid-myocardium of heart is generated, wherein the cell model is configured to simulate the performance of rise and fall of action potential of the cardiac cell using a differential equation. Further, a tissue model of a transmural section of one or more of a 2D ventricular tissue or a 3D ventricular tissue of the heart is generated using the cell model, wherein the 2D ventricular tissue is made of an array of cells interconnected by gap junction conductance (GJC). In the next step, a functionality of the gap junction conductance that allows passage of electric current between the M-cells using a plurality of conductive elements is modelled. In the next step, a plurality of properties of the M-cells is simulated, if all the cells in the mid-myocardium are considered to be M-cells, wherein the simulation includes a fivefold decrease in the GJC at an epi-mid mural junction along the whole length of the mid-myocardium, whereas there is no reduction in the GJC at the endo-mid interface. Similarly, a plurality of properties of a plurality of M-cell islands is also simulated, if each M-cell island is considered to be either located completely within the mid myocardium or partially in the endocardium layer. In the next step, the effect of physical characteristics of the M-cells is recorded on arrhythmogenesis by altering a position, a shape and a size of the M-cells in a plurality of configurations using the simulated M-cells and the plurality of properties of M-cell islands. Further, a pseudo-ECG is synthesized by exciting the tissues present in the tissue model, wherein the M-cells present in the tissue model get excited and stimulate neighboring cells by creating a convex wave-front travelling from the endocardium to epicardium and from an apex to a base of the heart. And finally, the effect of short QT syndrome is realized in the tissue model by changing a rectifying potassium current of M-cells to detect cardiac abnormality It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
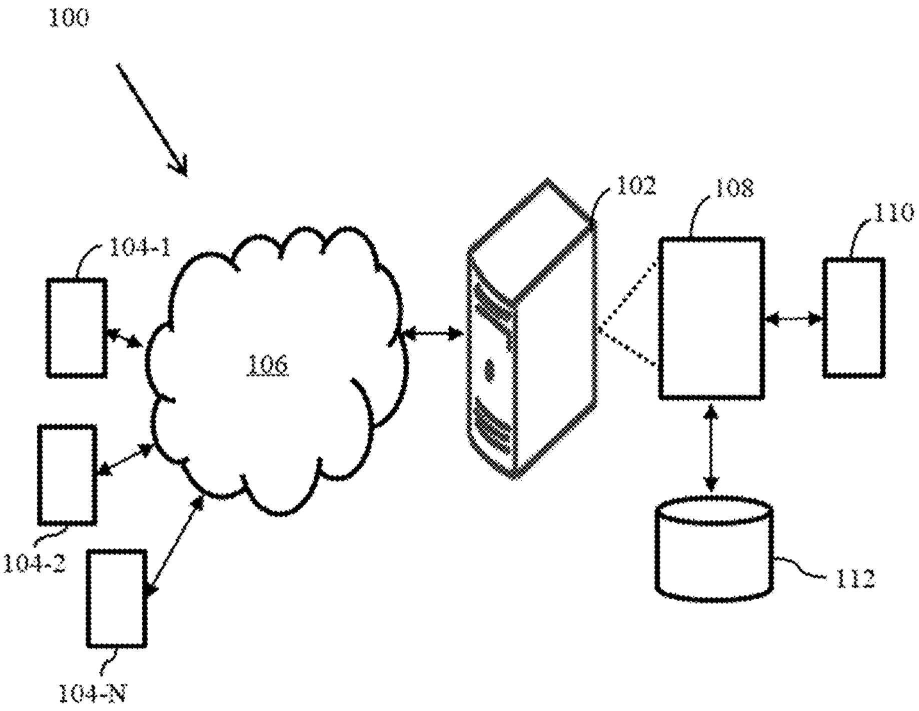
FIG. 1 illustrates an exemplary network diagram of a system for analyzing cardiac activity by modelling myocardial cells (M-cells) according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Currently, to visualize electrical activation pattern in the human heart, electro-anatomic mapping systems are utilized during catheter ablation surgeries. Understanding of arrhythmic phenomenon occurring in presence of various scenarios is mostly carried out in tissue or hearts explanted from animal models. Similarly, testing the effect of drugs is initially done through animal testing before coming into human clinical trials. To overcome this, computational modelling and simulation studies have been initiated as digital evidence for device and drug development.

However, inability to systematically link these interactions starting from molecular or cellular level to increasing levels of complexity like tissue such as genetics, development, function, environment, and evolution has led to partial advances in biological research across multiple spatial and temporal scales. The observed phenomena at various levels of complexity in cardiac system should be described mathematically. Also biologically meaningful information of cardiac system on morphological variation and genesis of these events to predict the effects of changing parameters of the model has multiple uses.

There are few a modelling and simulation tools existing in the prior art. One of the methods have developed a multiscale model incorporating electrophysiology, biomechanics and hemodynamics of the heart. However, it does not consider inclusion of M-cells. None of the existing techniques is able to simulate an exact physical and functional characteristics of these cells.

To bridge this important gap, a system and method has been provided for analyzing cardiac activity by modelling myocardial cells (M-cells). The method comprising preparing a computational tool that will allow biologists and physicians to analyze and retrieve cardiac cellular information automatically and enable discovering of relationships between cellular and cardiovascular system utilizing the cardiac M-cells.

Referring now to the drawings, and more particularly to FIG. 1 through FIG. 11, where similar reference characters denote corresponding features consistently throughout the figures, there are shown preferred embodiments and these embodiments are described in the context of the following exemplary system and/or method.

According to an embodiment of the disclosure, a network diagram of a system 100 for analyzing cardiac activity by modelling myocardial cells (M-cells) is shown in FIG. 1. The system 100 is configured to generate a model of the M-cells which takes into account the physical and functional characterization of M-cells, thereby allows to analyze the role of M-cells in genesis of T-wave morphology, arrhythmogenesis during genetic condition. The generated model can also be used to analyze the effect of drugs on the cardiac activity of the person.

According to an embodiment of the disclosure, the system 100 is configured to understand how the properties of M-cells affect the generation of T-wave and how they contribute to arrhythmogenesis in short QT syndrome 2 (SQTS2). A 2D transmural anisotropic ventricular model made up of endocardial (endo), mid-myocardial (mid) and epicardial (epi) cells is examined in which the electrical activity of each cell is modelled using a TP06 model. Different setups in which either the entire column of mid cells or an island of cells within the mid layer of the 2D transmural wall are considered as M-cells. Pseudo ECGs are created by exciting the tissue in order to analyze the morphology of the T-wave. Further a crucial role of M-cells in creating the morphology of the T-wave as well as promoting arrhythmogenesis under SQTS2 condition is analyzed which indirectly analyzed the cardiac activity.

According to an embodiment of the disclosure, it may be understood that the system 100 comprises one or more computing devices 102, such as a laptop computer, a desktop computer, a notebook, a workstation, a cloud-based computing environment and the like. It will be understood that the system 100 may be accessed through one or more input/output interfaces 104-1, 104-2, . . . , 104-N, collectively referred to as I/O interface 104 or user interface 104. Examples of the I/O interface 104 may include, but are not limited to, a user interface, a portable computer, a personal digital assistant, a handheld device, a smartphone, a tablet computer, a workstation and the like. The I/O interface 104 are communicatively coupled to the system 100 through a network 106.

In an embodiment, the network 106 may be a wireless or a wired network, or a combination thereof. In an example, the network 106 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 106 may include a variety of network devices, including routers, bridges, servers, computing devices, storage devices. The network devices within the network 106 may interact with the system 100 through communication links.

The system 100 may be implemented in a workstation, a mainframe computer, a server, and a network server. In an embodiment, the computing device 102 further comprises one or more hardware processors 108, one or more memory 110, hereinafter referred as a memory 110 and a data repository 112, for example, a repository 112. The memory 110 is in communication with the one or more hardware processors 108, wherein the one or more hardware processors 108 are configured to execute programmed instructions stored in the memory 110, to perform various functions as explained in the later part of the disclosure. The repository 112 may store data processed, received, and generated by the system 100.

The system 100 supports various connectivity options such as BLUETOOTH®, Universal serial bus (USB), ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

Figure 2:
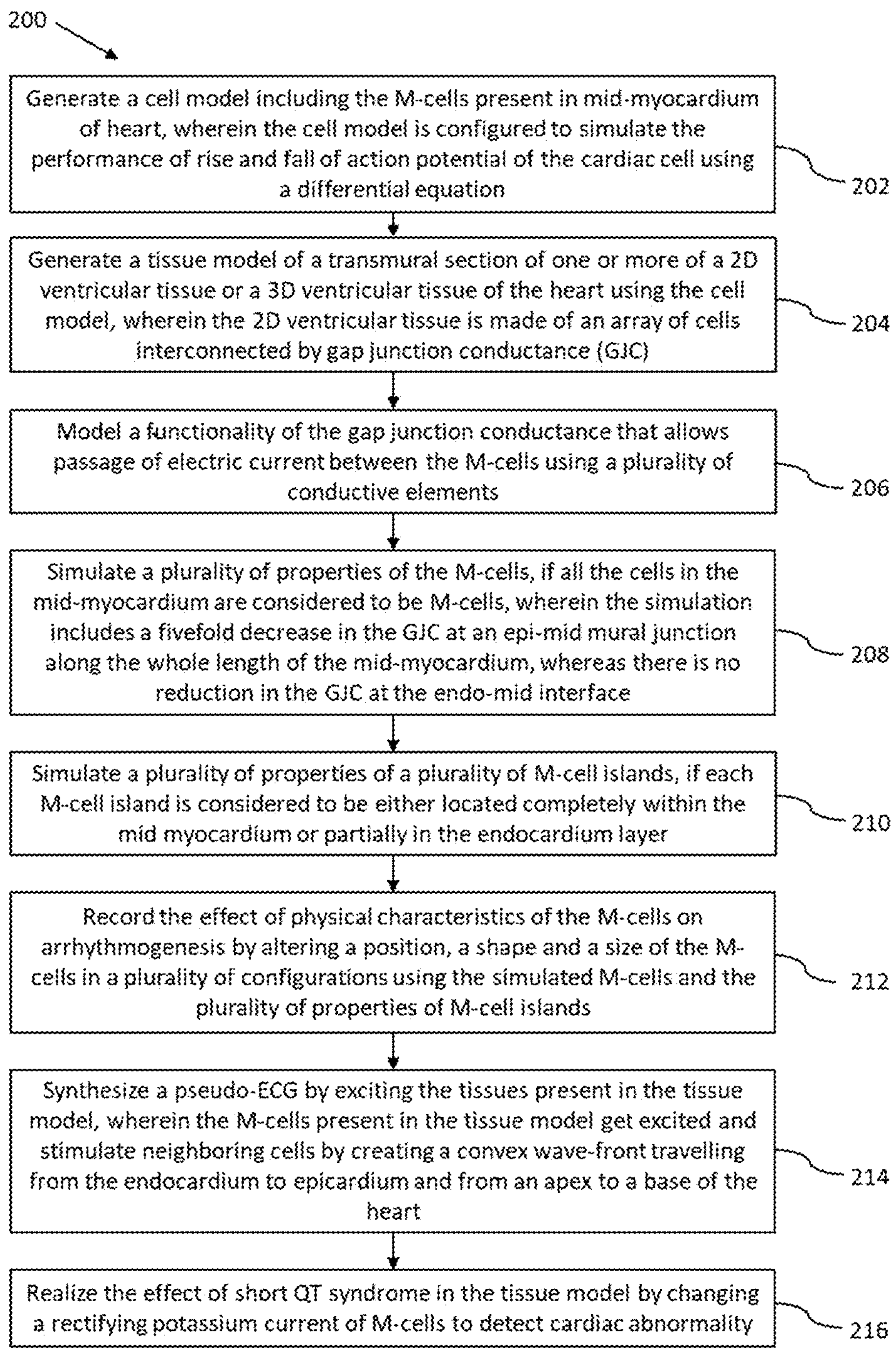
FIG. 2 is a flowchart of a method for analyzing cardiac activity by modelling myocardial cells (M-cells) according to some embodiments of the present disclosure.

In operation, a flow diagram of a method 200 for method for analyzing cardiac activity by modelling myocardial cells (M-cells) according to some embodiments of the present disclosure is shown in FIG. 2. The method 200 depicted in the flow chart may be executed by a system, for example, the system, 100 of FIG. 1. In an example embodiment, the system 100 may be embodied in a computing device.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 200 are described with help of system 100. However, the operations of the method 200 can be described and/or practiced by using any other system.

Initially at step 202 of the method 200, a cell model including the M-cells present in mid-myocardium of heart is generated. The cell model is configured to simulate the performance of rise and fall of action potential (AP) of a cell using a differential equation. The rise and fall of membrane potential in an individual cell is described by the differential equation below in equation (1)

$$C_m \frac{dV_m}{dt} = -(I_{ion} + I_{stim}) \tag{1}$$

where $V_m$ is a transmembrane potential, t is time, $C_m$ is a membrane capacitance, $I_{ion}$ is a summation of transmembrane ionic currents and $I_{stim}$ is an external current stimulus.

In an example, $I_{stim}$ has an amplitude of 52 mA and is applied for 1 ms in a TP06 model. The differential equations of the ionic parameters are integrated using Rush and Larsen scheme with a time step of 0.05 ms. The electrophysiological parameters for endo, mid and epi cells are taken from the TP06 model parameters. However, these original parameters from the TP06 model don't generate early after-depolarization (EAD) even when $G_{Kr}$ is reduced to 0. This drawback is overcome by modifying the following parameters in all cell types: (i) the time constant of the f-gate ($T_f$) of the L-type Ca current is decreased by a factor of two and (ii) the conductance of the Ca current ($G_{Cal}$) is increased by two fold.

Further at step 204, a tissue model of a transmural section of one or more of a 2D ventricular tissue or a 3D ventricular tissue of the heart is generated using the cell model. The heart could be an atlas heart or a personalized heart. The atlas heart means data and parameter derived or collected from open-source dataset or literature or unknown data poll. The personalized heart means-data and parameter will be extracted or estimated from the patient or an individual, for whom the cardiac analysis is performed The 2D ventricular tissue is made of an array of cells interconnected by gap junction conductance (GJC). Gap junction conductance is the interconnectivity between cells through which current passes. Variation of GJC implies an abnormality/disease condition like ischemia, etc. In an example, the transmural section of a 2D ventricular wall having a length of 5 cm and a thickness of 2 cm is considered for evaluation. This section is represented by an array of 250×100 cells in which the space between two cells is assumed to be 0.02 cm. The origin (Cell 1, 1) in this array of cells is taken as the bottom leftmost corner. The functionality of gap junctions (GJ) that allow the passage of electric current between cells is modelled using conductive elements. Ohm's law is used to describe this flow of current between two cells when there exists a difference in membrane voltage between them and it is represented as the same finite difference equation (2).

$$\begin{aligned} I_{stim} = {} & (V_{i-1,j-1} - V_{i,j})G_{i-1,j-1} + (V_{i-1,j} - V_{i,j})G_{i-1,j} + \\ & (V_{i-1,j+1} - V_{i,j})G_{i-1,j+1} + (V_{i,j-1} - V_{i,j})G_{i,j-1} + (V_{i,j+1} - V_{i,j})G_{i,j+1} + \\ & (V_{i+1,j-1} - V_{i,j})G_{i+1,j-1} + (V_{i+1,j} - V_{i,j})G_{i+1,j} + (V_{i+1,j+1} - V_{i,j})G_{i+1,j+1} \end{aligned} \tag{2}$$

where $I_{stim}$ is the current used to stimulate cell (i, j) and it is the sum of currents from the eight neighboring cells. Cells at the corner and perimeter of the array are coupled to 3 and 5 adjacent cells respectively. In the normal myocardial fibers, anisotropy exists with the longitudinal conduction being thrice as fast as the transverse conduction. To incorporate this property in the array, the GJC values along the length and width of the array are set to 4 µS and 0.4 µS respectively. These GJC values fall within the physiological range. These conduction values result in a conduction velocity of 76.9 cm/s and 33.3 cm/s through the length and width of the fiber respectively which matches the observed values. In this transmural tissue, two broad classifications are considered. The first classification in which all the cells in mid layer are considered to be M-cells and the second classification in which an island of M-cells is considered to be either located completely within the mid layer or partially in the endo layer.

At step 206 of method 200, the functionality of the gap junction conductance is modelled. The GJC allow the passage of electric current between M-cells using a plurality of conductive elements. Further a plurality of properties of M-cells is simulated depending on two conditions. In a first condition at step 208 of method 200, the plurality of properties of M-cells is simulated, if all the cells in mid-myocardium are considered to be M-cells. The simulation includes fivefold decrease in the GJC at an epi-mid mural junction along the whole length, whereas there is no reduction in GJC at the endo-mid interface.

It is known that a fraction of 40% endo, 30% mid and 30% epi with smaller apex APD than the basal APD, and got a good correspondence with the clinically observed ECG. Hence, in the first setup (TM-40), the transmural section is divided along the thickness from left to right into the same proportions. The transmural section is divided along the thickness from left to right into 25% endo, 35% mid and finally 40% epi cells. These percentages are also reported to get an upright T-wave in the ECG and have thus been considered for the second setup (TM-25) along with apex-base variation. In the third setup (TM-30), the transmural section is divided into 30% endo, 30% mid and finally 40% epi cells along with the apex-base variation. The % of cells in the different layers have been summarized in Table 1. The conductance of slow delayed rectifying potassium current $G_{Ks}$ value of endo cells is decreased to 92% of the actual TP06 value so that the APD of endo cells is greater than that of epi cells. The $G_{Ks}$ and $G_{to}$ values of the different cells are given in Table 2. A graded apex-base variation is introduced in endo cells by increasing the $G_{Ks}$ of apex to 1.5 times its base value. The values between apex to base are linearly interpolated. In the deep sub-epicardium, a decrease in tissue resistivity has been attributable to a sharp transition in cell orientation, reduced expression of connexin 43 and increased density of collagen in this region. It has been incorporated by decreasing the GJC by fivefold at the epi-mid mural junction. Likewise, a fivefold decrease in GJC at the epi-mid mural junction has been included along the whole length for a thickness of 5 cells (Cells 58 to 62) in all the three setups, whereas there is no reduction in GJC at the endo-mid interface.

TABLE 1

| Percentage of cells in the three setups of M-cell Layer Classification | | | |
|---|---|---|---|
| Setup | Endo Cells | M/Mid cells | Epi cells |
| TM-40 | 40 | 30 | 30 |
| TM-25 | 25 | 35 | 40 |
| TM-30 | 30 | 30 | 40 |

TABLE 2

| Variation in ionic parameters of different cells | | | |
|---|---|---|---|
| Parameters | Endo Cells | M/Mid cells | Epi cells |
| $G_{Ks}$ | 0.36064 nS/pF | 0.098 nS/pF | 0.392 nS/pF |
| $G_{to}$ | 0.073 nS/pF | 0.294 nS/pF | 0.294/pF |

Similarly, in a second condition at step 210, a plurality of properties of M-cell islands is simulated if an island of M-cells is considered to be either located completely within the mid-myocardium or partially in the endocardium layer.

M-cells have traditionally been defined as those having the largest APD, hence their $G_{Ks}$ value is taken as 0.098 nS/pF (same as used in TP06). The $G_{Ks}$ value of other cells is 0.392 nS/pF in TP06 model. When this same value is retained for epi cells and that of mid cells is reduced to 0.37632 nS/pF, it is observed that a positive T-wave doesn't occur. These $G_{Ks}$ values used for different cell types are listed in row 1 of Table.2. Hence, the same $G_{Ks}$ value is retained for mid cells while that of endo cells is reduced to 0.36064 nS/pF and that of epi cells is increased to 0.588 nS/pF so that there is a transition in APD among the layers with the epi cells having the smallest APD followed by the mid and endo cells. The $G_{to}$ values are taken from the TP06 model parameters. The base has been shown to have a larger APD compared to the apex, however the gradient of variation is small. These $G_{Ks}$ values used for different cell types are listed in row 2 of Table 3.

Figure 3:
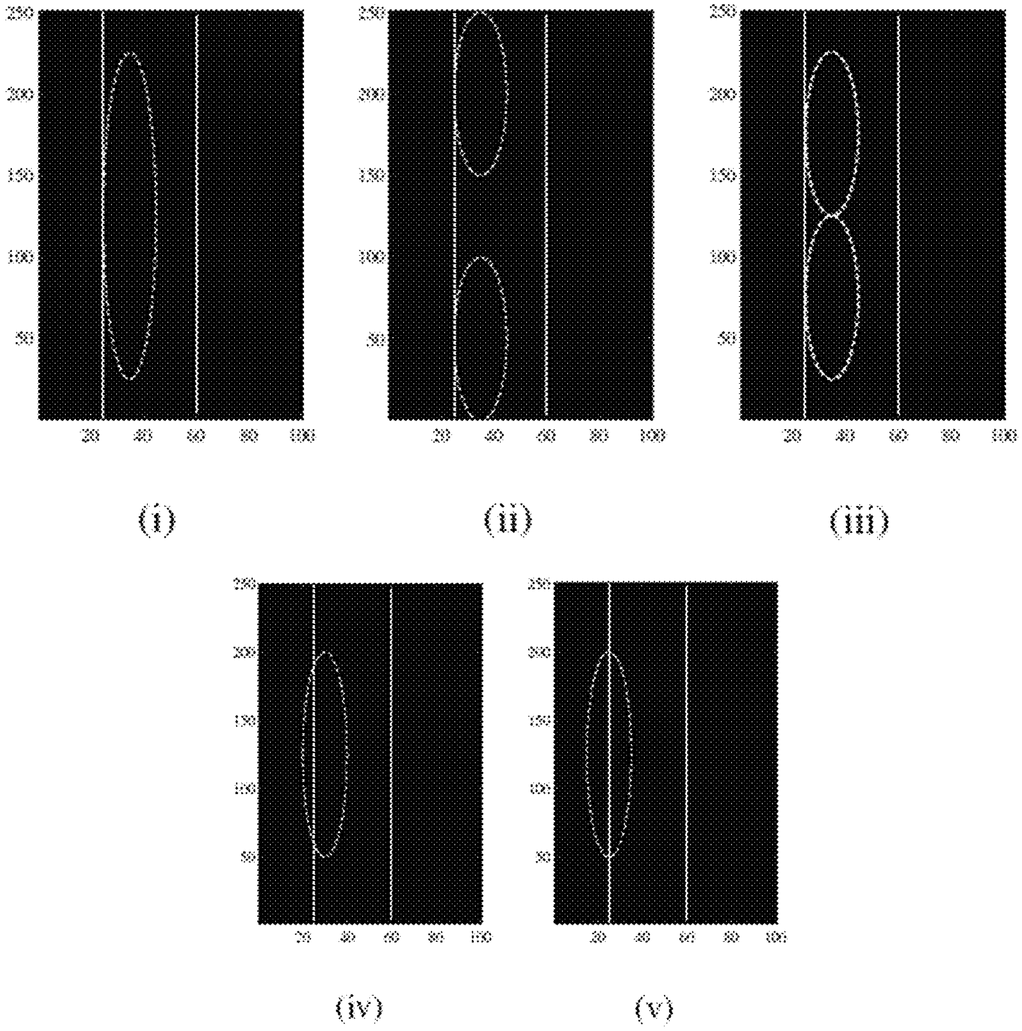
FIG. 3 illustrates various configurations of an M-cell island in accordance with some embodiments of the present disclosure.

According to an embodiment of the disclosure, the M-cell island is modelled as an ellipse positioned vertically with its center located in the mid layer at position (35, 125). Different sizes of the M-cell island are considered in which the minor axis is a constant of 10 pixels and the major axis is varied from 25 pixels to 50, 75 and 100 pixels respectively. These configurations are termed as 25M, 50M, 75M and 100M respectively. The 100M configuration is shown in FIG. 3(*i*). In order to understand the effect of physical characteristics of the M-cells on arrhythmogenesis, the position, shape and size of the M-cells are altered in different configurations as described in FIG. 3. The position of the M-cell island is changed by moving the elliptical island of major axis 75 pixels and minor axis 10 pixels to top position (35, 75) and bottom position (35,175). The shape of the M-cell island is altered by increasing the minor axis to 15 pixels and the major axis is again varied from 25 pixels to 50, 75 and 100 pixels respectively. These configurations are termed as Horz-25M, Horz-50M, Horz-75M and Horz-100M.

The apex to base variations which was till now only included in the endo layer in now either introduced in the epi layer or mid layer only. The GKs values considered at base and apex are listed in rows 3 and 4 of Table.3 respectively. The values in between apex and base are linearly interpolated. These four configurations are termed as EndoAB2, EndoAB1, EpiAB and MidAB. In place of a single M-cell island, two M-cell islands were placed in the mid layer. A combination of different sizes and locations are simulated. The different sizes and locations at which the islands are placed are given in the following:

- $25M^2_{center2}$: Two M-cell islands with an ellipse of major axis 25 and minor axis 10 located at center (35, 25) and (35, 225).
- $25M^2$: Two M-cell islands with an ellipse of major axis 25 and minor axis 10 located at center (35, 75) and (35, 175).
- $50M^2_{center2}$: Two M-cell islands with an ellipse of major axis 50 and minor axis 10 located at center (35, 50) and (35, 200). (As shown in FIG. 3(*ii*))

TABLE 3

| $G_{Ks}$ values of different cell types in different configurations | | | | |
|---|---|---|---|---|
| Setup | Endo cells | Mid cells | Epi cells | M cells |
| EndoAB2 | 0.36064 nS/pF (Base) to 0.54096 nS/pF (Apex) | 0.37632 nS/pF | 0.392 nS/pF | 0.098 nS/pF |
| EndoAB1 | 0.36064 nS/pF (Base) to 0.54096 nS/pF (Apex) | 0.392 nS/pF | 0.588 nS/pF | 0.098 nS/pF |
| EpiAB | 0.36064 nS/pF | 0.392 nS/pF | 0.392 nS/pF (Base) to 0.588 nS/pF (Apex) | 0.098 nS/pF |
| MidAB | 0.36064 nS/pF | 0.36064 nS/pF (Base) to 0.392 nS/pF (Apex) | 0.588 nS/pF | 0.098 nS/pF |

Further at step 212, the effect of physical characteristics of the M-cells on arrhythmogenesis is recorded by altering the position, shape and size of the M-cells in a plurality of configurations using the simulated M-cells and M-cell island properties.

- $50M^2$: Two M-cell islands with an ellipse of major axis 50 and minor axis 10 located at center (35, 75) and (35, 175). (As shown in FIG. 3(*iii*))
- $75M^2$: Two M-cell islands with an ellipse of major axis 75 and minor axis 10 located at center (35, 75) and (35, 175).

Further, M-cell islands are present in the deep sub-endocardium. Hence, the M-cell island is partially placed in endo-mid layers. An M-cell elliptical island with major axis 50 and minor axis 10 is located at center (30, 125) and then shifted further into the endo island with center at (25, 125). The percentage of M-cells in the endo layer are 33% and 50% respectively. The major axis of the M-cell island is increased 75 pixels and placed at the same centers. These configurations are termed as 50Mendo1, 50Mendo2, 75Mendo1 and 75Mendo2. The last two configurations are illustrated in FIG. 3(*iv*) and FIG. 3(*v*). Further, this island was also moved to the top and bottom position to test its effect on pseudo ECG.

At step 214, a pseudo ECG is synthesized by exciting the tissues present in the tissue model. The M-cells present in the tissue model get excited and stimulate the neighboring cells by creating a convex wave-front travelling from the endocardium to epicardium and from the apex to the base of the heart. The ventricular tissue is paced at a cycle length (CL) of 800 ms corresponding to a heart rate of 75 beats/min until all the TP06 variables reach steady state. A cluster of 10×2 endo cells (Cells 1:10, 1:2) in the left bottom most corner of the tissue is considered as the normal pacing region. The cells in this region get excited and stimulate the neighbouring cells creating a convex wave front travelling from the endo to epi layer and from the apex to the base. Pseudo-ECGs are created from the 2D tissue according to the equations (3) and (4).

$$\Phi_e(x', y', z') = \int\int\int\left[-\nabla V_m\left(\nabla\frac{1}{r}\right)\right]dxdydz \tag{3}$$

$$r = \left[(x-x')^2 + (y-y')^2 + (z-z')^2\right]^{\frac{1}{2}} \tag{4}$$

where $\nabla V_m$ is the spatial gradient of voltage and r is the distance from a source point (x, y, z) to a field point (x', y', z'). Every point in the grid is considered as a source point while three field points $P_1$ (95, 25, 50), $P_2$ (10, 75, 50) and $P_3$ (10, 225, 50) are chosen on a plane at a distance of 1 cm parallel to the ventricular tissue in the positive z axis to build an Einthoven triangle. The voltage difference between $P_1$ and $P_2$, $P_1$ and $P_3$ and $P_2$ and $P_3$ form the three ECG leads. The ECG is normalized and the lead with the highest voltage amplitude ($P_1$ and $P_3$) is used for further study. Until now, the composition of the tissue under normal conditions and synthesis of pseudo ECG from this tissue has been described.

And finally at step 216, the effect of short QT syndrome (SQTS) is realized in the tissue model by changing a rectifying potassium current of M-cells to detect cardiac abnormality. The rectifying potassium current is an ionic parameter that modulates the shape and duration of action potential. The effect of short QT syndrome type 2 is realized in the model by changing the $I_{Ks}$ current of all types of cells. The parameters of equations for $I_{Ks}$ current in the TP06 model are modified based on the experimental data on SQT2 KCNQ1 V307L. Four different cases: wild type (WT), heterozygous (het), homozygous (hom) and homozygous reduced (homred) are considered for KCNQ1 V307L mutation induced changes. Among these, only the heterozygous mutation is considered here as this assumes a 50:50 mixture of WT and mutant KCNQ1 subunits and has been shown to sustain reentrant arrhythmia. The equation for time constant of $x_s$-gate of $I_{Ks}$ current is different for M-cells compared to the other cells since the M-cells have a reduced $I_{Ks}$ current. These equations are given below in equation (5), (6) and (7):

Heterozygous mutant expression (Het):

$$x_{s\infty} = \frac{1}{\left(1 + e^{(-20.62 - V_m)/10.96}\right)} \tag{5}$$

For M cells $$\tau_{xs} = 0.75 * (\alpha_{xs}\beta_{xs} + 80) \tag{6}$$

else $$\tau_{xs} = 0.7 * (\alpha_{xs}\beta_{xs} + 80) \tag{7}$$

Further, the $I_{Ks}$ current in epicardial cells is scaled by a factor of 1.5 compared to mid-myocardial cells, so as to generate a high, symmetrical T-wave as observed in clinical ECG under SQTS conditions. The normal pacing site at the lower left most corner of the tissue is excited at the normal heart rate of 75 beats/min. After all the variables reach steady state, the tissue is now paced at a shorter cycle length (CL) of 350 ms which is representative of premature beats to induce a ventricular arrhythmic pattern. After certain number of such premature beats, the normal pacing CL of 800 ms is resumed. The normalized pseudo ECG is then created from the tissue. The tissue activity is recorded for a total duration of 10 s to serve as a digital evidence for cardiac abnormality detection.

According to an embodiment of the disclosure, the system and method for analyzing cardiac activity by modelling myocardial cells (M-cells) can be validated with the help of following numerical results.

On simulating the group of cells in the lower leftmost corner (Cells 1:10, 1:2) of the tissue, a convex wave front propagates from the endo to mid and epi layer from the bottom to the top of the tissue. The repolarization occurs in the epi and endo layer and the M-cells in the mid layer are the last to repolarize. The pseudo ECGs synthesized from the above-mentioned different M-cell configurations is described as follows.

Figure 4:
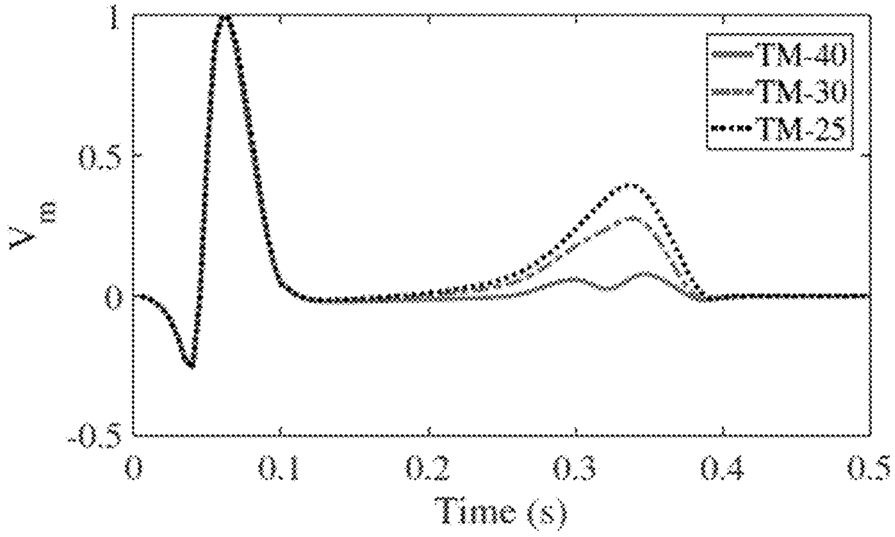
FIG. 4 is graphical representation of a pseudo ECG for three different transmural percentages according to some embodiments of the present disclosure.

FIG. 4 shows the pseudo ECGs for the three different setups explained earlier. When the percentage of cells in the different layers is varied, the shape of the T-wave is observed to change. The higher percentage of epi cells in TM-40 is observed to give rise to a low amplitude (0.059 mV and 0.078 mV) notched pattern of T-waves which are usually found to be symptomatic in hypokalemia condition or long QT syndrome type 2. The peak amplitudes of the T-wave in TM-25 and TM-30 is found to 0.3949 mV and 0.2776 mV respectively. Due to the higher peak value of T-wave obtained in TM-25 setup, the same proportion of cells is used for further analysis. The $T_{end}$ for the three setups: TM-25, TM-30 and TM-40 occurs at almost the same time instant of 0.41 s, 0.39 s and 0.405 s. The results obtained here for the different percentages obtained for the transmural layers. The results showed that the TM-40 A1:5 B1 configuration showed good agreement with the clinically observed results, while in the present disclosure, the same configuration, gave rise to a notched T-wave. This may be due to differences in the 2D structure considered as well as a reduction in GJC considered in the mid-epi layer.

M-Cell Islands

Figure 5:
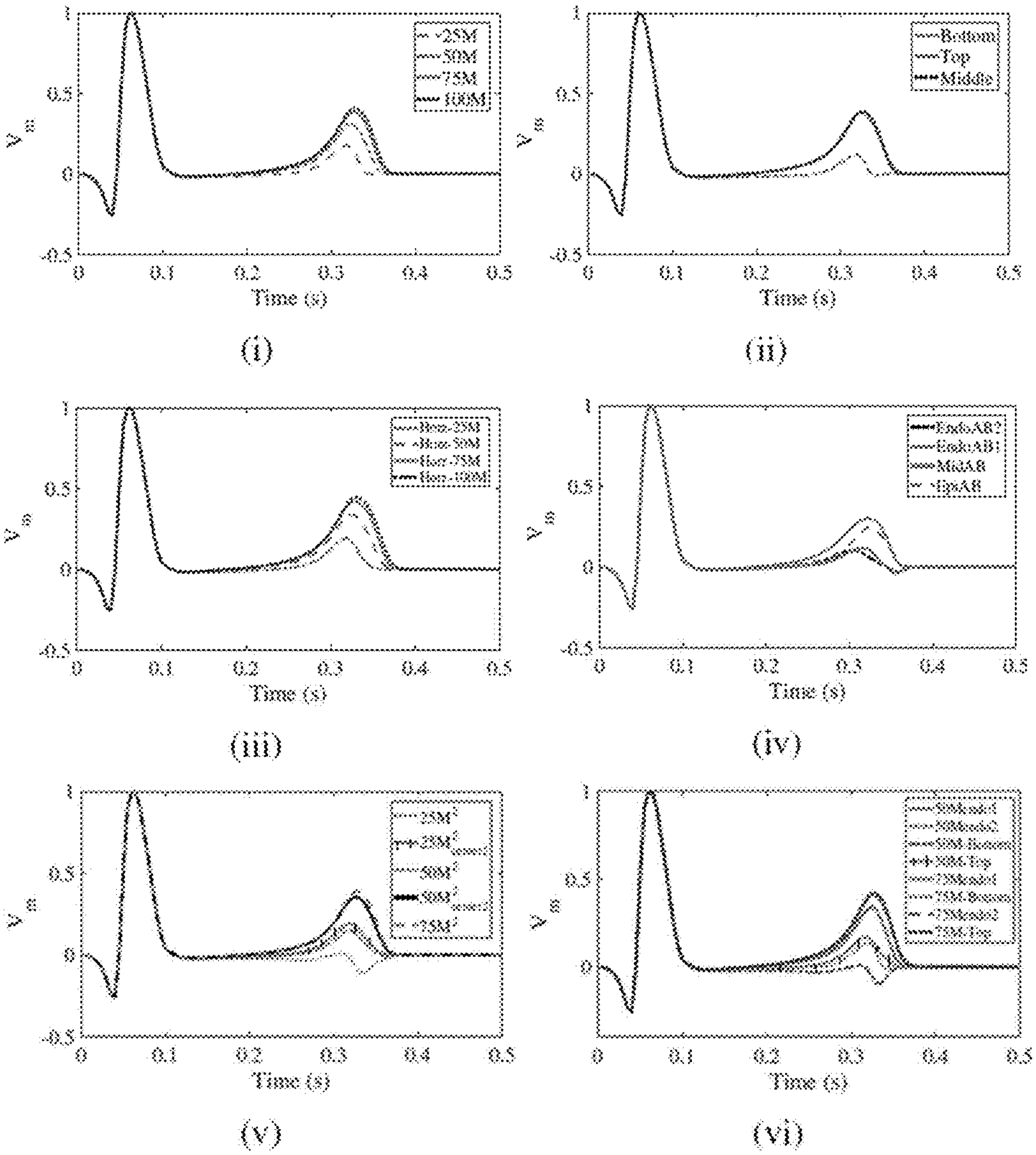
FIG. 5 is normalized pseudo ECGs generated on varying (i) Size, (ii) Position, (iii) Shape, (iv) Apex-Base properties and on introducing, (v) Two M-cell islands in mid layer and (vi) M-cell in endo-mid layer in accordance with some embodiments of the present disclosure.

The pseudo ECG generated for the various configurations are shown in FIG. 5. It is observed that as the major axis of the M-cell island is varied from 25 to 50 to 75 and to 100, the T-peak value is 0.1771 mV, 0.312 mV, 0.3894 mV and 0.41 mV respectively. Further, the end of the T-wave is also increased from 0.345 s, 0.375 s, 0.38 s and 0.39 s respectively as seen in FIG. 5(*i*). This shows that as the number of M-cells increases, the time taken for it to completely repolarize increases and therefore this causes the T-end to get lengthened. When the pseudo ECG patterns obtained for the different positions of the M-cell island centered in locations (35, 75), (35, 125) and (35, 175) are compared from FIG. 5(*ii*), it is observed that the T peak is almost similar for the top and middle locations about 0.3826 mV and 0.3894 mV respectively whereas for the lower position at (35, 175), the T-peak value is 0.1233 mV. The T-end values for the three positions are 0.385 s, 0.38 s and 0.34 s respectively. Placement of M-cell island in the top or middle position produced almost similar T-peak amplitude and duration while in the bottom position they have a reduced amplitude and duration. This may be because the depolarization pattern is from the bottom to the top of the tissue and hence these M-cells would get excited earlier and return to their resting state also earlier.

When the minor axis of the M-cell island is changed to 15 pixels and the major axis is changed to different values of 25, 50, 75 and 100 pixels, the T-peak value increases from 0.1948 mV, 0.3403 mV, 0.422 mV and 0.4455 mV as seen in FIG. 5(*iii*). The T-end values are 0.36 s, 0.375 s, 0.38 s and 0.385 s respectively. The same observation of increasing the size of the M-cell island has an effect on increasing the T-peak and T-end values.

In Endo AB1 configuration, a positive T-wave peak of 0.3007 mV is observed. In EndoAB2 configuration, a biphasic T-wave with a positive peak value of 0.1046 mV and a negative peak value of −0.029 mV is shown in FIG. 5(*iv*). This pseudo ECG is characteristic during ischemic condition. If apico-basal variation in included in the epi layer: EpiAB configuration, the pseudo ECG obtained is also concordant although with a lower peak amplitude of 0.2465 mV. However, in the midAB configuration with apico-basal variation in the mid layer, a biphasic T-wave with a positive peak value of 0.1179 mV and a negative peak value of −0.03 mV is observed in the ECG similar to that seen in EndoAB2. The T-end is same in all the configurations and occurs at 0.375 s. Apico-basal (AB) electrical heterogeneity has been shown to exist in the canine and human ventricular myocardium. In the present disclosure, it is included in the mid and epi layer to understand its effect on the generation of T-waves. Mid AB gives rise to a biphasic T-wave while endo or epi AB gives rise to concordant T-waves. M-cell islands in the epicardial positions are not tested as most of the experimental observations report the presence of M-cells in the mid-myocardium closer to the deep sub-endocardium.

In the $25M^2$ configuration, a biphasic T-wave pattern with a positive peak value of 0.012 mV and a negative peak value of −0.1116 mV is observed in FIG. 5(*v*). The Tend occurs at 0.375 s. When these two M-cell are shifted to different centers in the $25M^2_{center2}$, a positive T-peak of 0.1947 mV is seen and T-end is at 0.365 s. The size of the islands are increased to 50 pixels in the $50M^2$ configuration, here the T-peak value is 0.1517 mV and T-end is 0.36 s. In the $50M^2_{center2}$ configuration, the T-peak value is 0.3563 mV and T-end is 0.38 s. In the $75M^2$ configuration, the T-peak is 0.3889 mV and T-end is 0.38 s. Thus, when two M-cell islands are placed in the mid layer, it is observed that the T-wave amplitude is higher when the two islands are placed close together than when they are placed further apart.

The placement of M-cell island in the endo layer in both the configurations: 75Mendo1 and 75Mendo2 has almost similar T-peak value of 0.4185 mV and T-end value of 0.375 s as seen in FIG. 5(*vi*). When this M-cell island is moved to the top position, the T-peak slightly decreases to 0.4137 mV while the T-end is the same value of 0.375 s. Placing the same island in the bottom position reduces the T-peak to 0.1367 mV and T-end to 0.345 s. Similarly, the reduced size of the M-cell island: 50Mendo1 and 50Mendo2 configuration also have similar values of 0.3416 mV and 0.3359 mV respectively. The T-end is the same value of 0.37 s for both cases. When these islands are moved to the top position (30, 75), the T-peak has a significantly lower value of 0.1692 mV and T-end is 0.365 s. However, placement of M-cell island in the bottom position (30,175) creates a biphasic type of T-wave with positive peak value of 0.0095 mV and negative peak value of −0.095 mV and T-end value of 0.36 s. The shifting the M-cells slightly into the endocardial border increases the amplitude of the T-waves. Similarly, here it is observed that the T-wave amplitude is increased when the M-cell island is moved from the mid layer slightly into the endo layer. Further, movement of the island into the endo layer such that the M-cell island is placed in the middle of the endo-mid layer causes the T-wave amplitude to remain the same. Placement of the M-cell island in the lower position of mid layer creates a T-peak of lower amplitude or a biphasic T-wave. Among the different configurations considered, some of them gave rise to concordant T-wave although with different peak amplitudes and duration while few others resulted in a notched or biphasic T-wave. These notched or biphasic waves are generally found in pathologies in which the ventricular repolarization sequence is altered.

Short QT Syndrome

Among the various configurations of tissue considered for evaluation, only certain configurations generate a positive T-wave peak. Hence, these are considered further for studying which type of tissue is vulnerable to arrhythmia under SQTS2 conditions. Heterozygous mutation is introduced in all the cells of the tissue and premature beats (PBs) are introduced in between the normal pacing pulses to generate an arrhythmia. Single or two PBs don't generate an arrhythmia. Hence, three PBs are introduced in between the normal pacing pulse.

M-Cell Layer: TM25 Configuration

Figure 6:
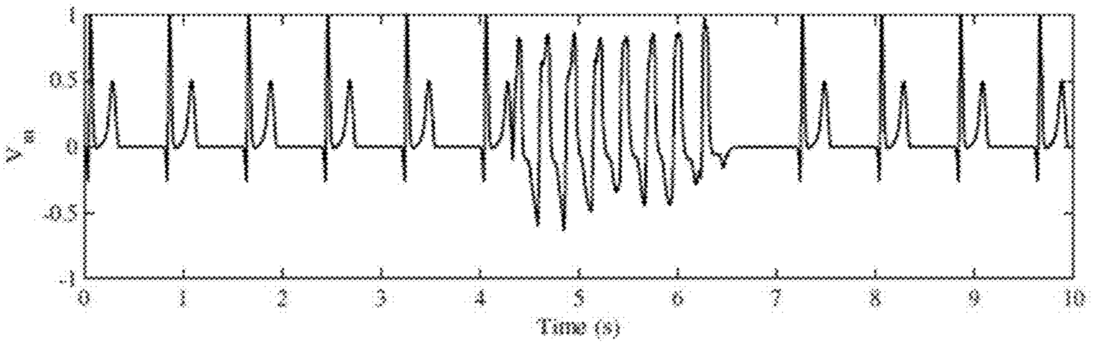
FIG. 6 shows a pseudo ECG in TM25 configuration and heterozygous mutation in accordance with some embodiment of the present disclosure.

In the TM-25 configuration, after six normal pacing pulses of 800 ms, three premature beats of 270 ms are applied in order to generate an arrhythmia. FIG. 6 shows the pseudo ECG and voltage snapshots on application of this pacing protocol. In the normalized pseudo ECG, it is observed that the first six beats are normal and appear at regular intervals of 800 ms. The peak amplitude of the first beat is 0.4977 mV and the QT interval is 0.305 ms. The three premature beats are applied at 4.27 s, 4.54 s and 4.81 s, after which an arrhythmic type of pattern is observed that is not sustained. After a long pause, the normal pacing pulse is resumed at 7.2 s.

M-Cell Layer: TM30 Configuration

Figure 7:
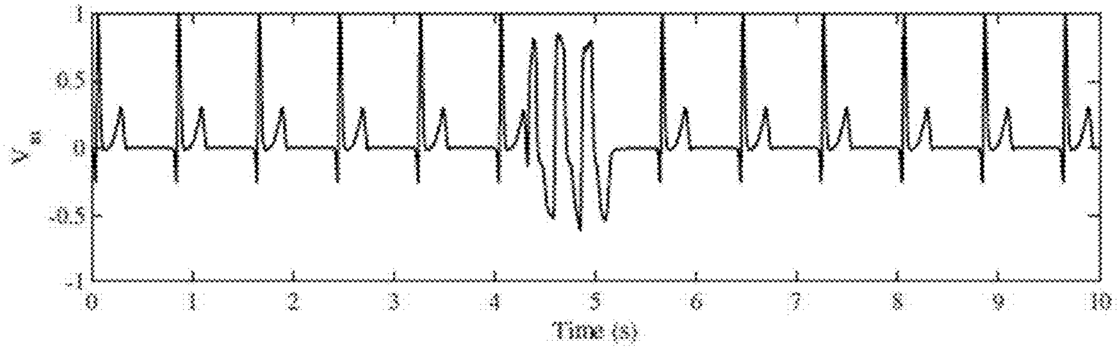
FIG. 7 shows a pseudo ECG in TM30 configuration and heterozygous mutation in accordance with some embodiment of the present disclosure.

In the TM-30 configuration, the heterozygous mutation is incorporated in all cells and the tissue is paced with the same pacing protocol. The generated normalized pseudo ECG is shown in FIG. 7. After six normal pacing pulses, three PBs are applied. The T-peak is 0.3035 mV and QT interval is 0.30s. It is observed that the three beats give rise to an arrhythmia type pattern but this is not sustained and the normal pacing sequence is resumed at 5.6 s.

M-Cell Island

Figure 8:
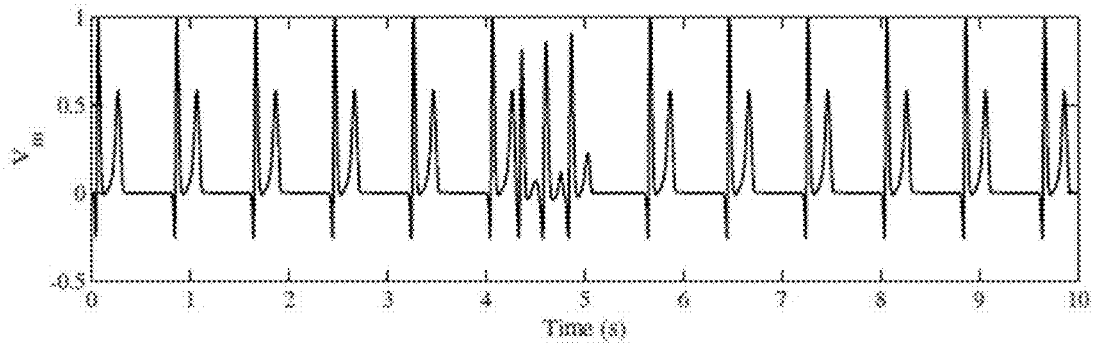
FIG. 8 shows a pseudo ECG in M-cell island configuration and heterozygous mutation in accordance with some embodiment of the present disclosure.

In the M-cell island configuration: M75, heterozygous gene mutation of SQTS2 conditions are introduced and the same pacing protocol of premature beats each of 260 ms are applied in between the normal pacing pulses. FIG. 8 shows the normalized pseudo ECG and voltage snapshots of this M-cell configuration on applying this same pacing protocol. In the pseudo ECG, it is seen that the peak value of the first QRS complex is 0.581 mV and QT interval is 0.28 s. After six normal pacing pulses, the three premature beats are applied at 4.26 s, 4.52 s and 4.78 s. The application of three PBs doesn't generate an arrhythmic rhythm and the normal pacing sequence is resumed after a pause at 5.6 s.

Two M-Cell Islands

Figure 9:
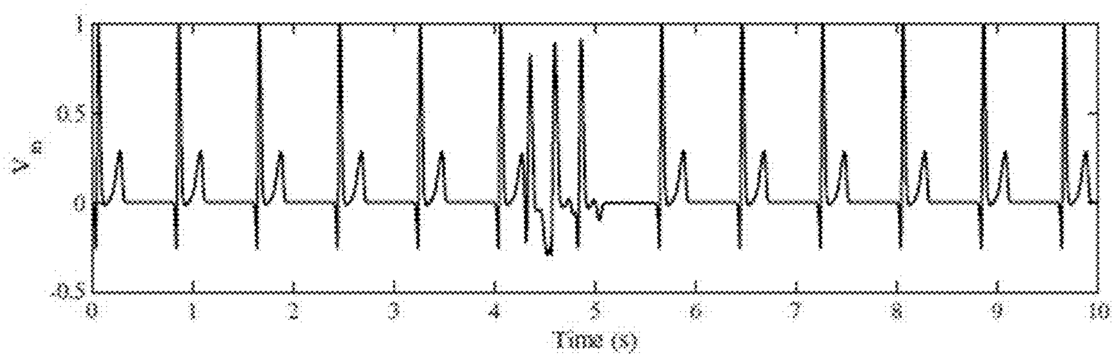
FIG. 9 shows a pseudo ECG in two M-cells configuration and heterozygous mutation in accordance with some embodiment of the present disclosure.

In presence of two M-cell islands having minor axis 10 and major axis of 50 pixels located at centers (35, 75) and (35, 175), the heterozygous gene mutation and same pacing protocol described in last section is applied. FIG. 9 shows the pseudo ECG generated from the tissue. Here also, it is observed that after the three PBs, no arrhythmic activity is generated and the normal pacing pulse is resumed at 5.6 s. The T-peak of the first beat is 0.2875 mV and QT interval is 0.28 ms.

M-Cell in Endo Layer

Figure 10:
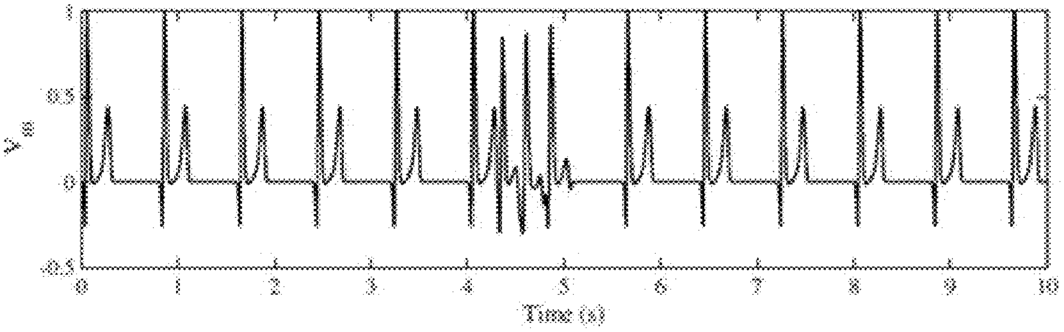
FIG. 10 shows a pseudo ECG in two M-cell in endo configuration and heterozygous mutation in accordance with some embodiment of the present disclosure.

With the M-cell located partially in the endo layer, the same conditions of SQTS2 heterozygous mutation and pacing sequence are applied. The pseudo ECG in FIG. 10 shows that after six normal pacing pulses, the three PBs don't generate an arrhythmia and the regular pacing sequence is resumed at 5.6 s. The T-peak value is 0.438 mV and QT interval is 0.28 s.

M-Cell Island with EpiAB

Figure 11:
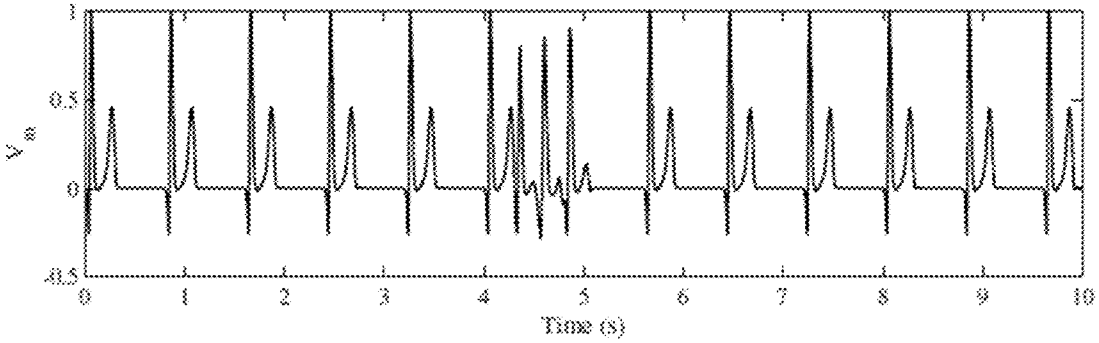
FIG. 11 shows a pseudo ECG in two M-cell in epiAB configuration and heterozygous mutation in accordance with some embodiment of the present disclosure.

In place of apex-base variation at the endo layer, it is introduced at the epi layer to see its effect on the generation of reentry under SQTS2 conditions. The pseudo-ECG in FIG. 11 shows that on applying 3 PBs in between the normal pacing pulses, no arrhythmic activity is generated. The T-peak value of the first beat is 0.4574 mV and QT interval is 0.28 ms.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiment of present disclosure herein addresses unresolved problem of role of M-cells and their effort, to be very specific the functional and structural characteristics of M-cells in relation to the surrounding endocardial, epicardial and mid-myocardial cells. The embodiment thus provides a method and system of analyzing the properties of M-cells and its relation to other cells which are difficult to understand using conventional experimental methods like in-silico studies due to the unique positioning of these cells in between the endo and mid layers. Moreover, the embodiments herein further provide a method and system for analyzing cardiac activity by modelling the cardiac cell with myocardial cells (M-cells).

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), readonly memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for analyzing cardiac activity by modelling cardiac cells with myocardial cells (M-cells), the method comprising:

generating, via one or more hardware processors, a cell model including the M-cells present in a mid-myocardium of heart, wherein the cell model is configured to simulate a performance of a rise and fall of action potential of the cardiac cell using a differential equation;

generating, via the one or more hardware processors, a tissue model of a transmural section of one or more of a 2D ventricular tissue or a 3D ventricular tissue of the heart using the cell model, wherein the 2D ventricular tissue is made of an array of cells interconnected by gap junction conductance (GJC);

modelling, via the one or more hardware processors, a functionality of the gap junction conductance that allows passage of electric current between the M-cells using a plurality of conductive elements, wherein a variation in the GJC implies an abnormal condition;

simulating, via the one or more hardware processors, a plurality of properties of the M-cells, if all the cells in the mid-myocardium are considered to be M-cells, wherein the simulation includes a fivefold decrease in the GJC at an epi-mid mural junction along the whole length of the mid-myocardium, whereas there is no reduction in the GJC at a endo-mid interface;

simulating, via the one or more hardware processors, a plurality of properties of a plurality of M-cell islands, if each M-cell island is considered to be either located completely within the mid-myocardium or partially in a endocardium layer;

recording, via the one or more hardware processors, a effect of physical characteristics of the M-cells on arrhythmogenesis by altering a position, a shape and a size of the M-cells in a plurality of configurations using the simulated M-cells and the plurality of properties of M-cell islands, wherein the each of the plurality of M-cell Islands is modelled as an ellipse positioned vertically with an associated center located in a mid-layer, wherein different sizes of the plurality of M-cell islands are considered in which a minor axis is a constant of ten pixels and a major axis is varied from 25 pixels to 50, 75 and 100 pixels respectively, wherein the position of the plurality of M-cell islands is altered by moving an elliptical island of the major axis 75 pixels and the minor axis 10 pixels to top position and bottom position, and the shape of the plurality of M-cell islands is altered by increasing the minor axis to 15 pixels and the major axis is again varied from 25 pixels to 50, 75 and 100 pixels respectively;

synthesizing, via the one or more hardware processors, a pseudo-ECG by exciting the tissues present in the tissue model, wherein the M-cells present in the tissue model get excited and stimulate neighboring cells by creating a convex wave-front travelling from the endocardium to epicardium and from an apex to a base of the heart; and realizing, via the one or more hardware processors, an effect of short QT syndrome in the tissue model by changing a rectifying potassium current of M-cells to detect cardiac abnormality, wherein the potassium current in epicardial cells is scaled by a pre-defined factor to generate a high, symmetrical T-wave as observed in clinical ECG under short QT syndrome (SQTS) conditions.

2. The method of claim 1 wherein an origin of the array of cells is taken as a bottom leftmost corner.

3. The method of claim 1, wherein the flow of current between two cardiac cells is described using Ohm's law, when there exists a difference in membrane voltage between them.

4. The method of claim 1, wherein two M-cell islands are placed in the mid layer, wherein each of the two M-cell islands is an ellipse with a major axis of 25 pixels and a minor axis of 10 pixels, further wherein each of the two M-cell islands is located at two distinct centers.

5. The method of claim 1, wherein the heart is one of an atlas heart or a personalized heart.

6. The method of claim 1, wherein the differential equation is represented as:

$$C_m \frac{dV_m}{dt} = -(I_{ion} + I_{stim})$$

where $V_m$ is a transmembrane potential, t is time, $C_m$ is a membrane capacitance, $I_{ion}$ is a summation of transmembrane ionic currents and $I_{stim}$ is an external current stimulus.

7. A system for analyzing cardiac activity by modelling the cardiac cells with myocardial cells (M-cells), the system comprises:

an input/output interface;

one or more hardware processors;

a memory in communication with the one or more hardware processors, wherein the one or more first hardware processors are configured to execute programmed instructions stored in the one or more first memories, to:

generate a cell model including the M-cells present in a mid-myocardium of heart, wherein the cell model is configured to simulate a performance of a rise and fall of action potential of the cardiac cell using a differential equation;

generate a tissue model of a transmural section of one or more of a 2D ventricular tissue or a 3D ventricular tissue of the heart using the cell model, wherein the 2D ventricular tissue is made of an array of cells interconnected by gap junction conductance (GJC);

model a functionality of the gap junction conductance that allows passage of electric current between the M-cells using a plurality of conductive elements, wherein a variation in the GJC implies an abnormal condition;

simulate a plurality of properties of the M-cells, if all the cells in the mid-myocardium are considered to be M-cells, wherein the simulation includes a fivefold decrease in the GJC at an epi-mid mural junction along the whole length of the mid-myocardium, whereas there is no reduction in the GJC at a endo-mid interface;

simulate a plurality of properties of a plurality of M-cell islands, if each M-cell island is considered to be either located completely within the mid-myocardium or partially in a endocardium layer;

record an effect of physical characteristics of the M-cells on arrhythmogenesis by altering a position, a shape and a size of the M-cells in a plurality of configurations using the simulated M-cells and the plurality of properties of M-cell islands, wherein the each of the plurality of M-cell Islands is modelled as an ellipse positioned vertically with an associated center located in a mid-layer, wherein different sizes of the plurality of M-cell islands are considered in which a minor axis is a constant of ten pixels and a major axis is varied from 25 pixels to 50, 75 and 100 pixels respectively, wherein the position of the plurality of M-cell islands is altered by moving a elliptical island of the major axis 75 pixels and the minor axis 10 pixels to top position and bottom position, and the shape of the plurality of M-cell islands is altered by increasing the minor axis to 15 pixels and the major axis is again varied from 25 pixels to 50, 75 and 100 pixels respectively;

synthesize a pseudo-ECG by exciting the tissues present in the tissue model, wherein the M-cells present in the tissue model get excited and stimulate neighboring cells by creating a convex wave-front travelling from the endocardium to epicardium and from an apex to a base of the heart; and realize an effect of short QT syndrome in the tissue model by changing a rectifying potassium current of M-cells to detect cardiac abnormality, wherein the potassium current in epicardial cells is scaled by a pre-defined factor to generate a high, symmetrical T-wave as observed in clinical ECG under short QT syndrome (SQTS) conditions.

8. The system of claim 7, wherein an origin of the array of cells is taken as a bottom leftmost corner.

9. The system of claim 7, wherein the flow of current between two cardiac cells is described using Ohm's law, when there exists a difference in membrane voltage between them.

10. The system of claim 7, wherein two M-cell islands are placed in the mid layer, wherein each of the two M-cell islands is an ellipse with a major axis of 25 pixels and a minor axis of 10 pixels, further wherein each of the two M-cell islands is located at two distinct centers.

11. The system of claim 7, wherein the heart is one of an atlas heart or a personalized heart.

12. One or more non-transitory machine-readable information storage mediums comprising one or more instructions which when executed by one or more hardware processors cause:

generating, a cell model including the M-cells present in a mid-myocardium of heart, wherein the cell model is configured to simulate a performance of a rise and fall of action potential of the cardiac cell using a differential equation;

generating, via the one or more hardware processors, a tissue model of a transmural section of one or more of a 2D ventricular tissue or a 3D ventricular tissue of the heart using the cell model, wherein the 2D ventricular tissue is made of an array of cells interconnected by gap junction conductance (GJC);

modelling, via the one or more hardware processors, a functionality of the gap junction conductance that allows passage of electric current between the M-cells using a plurality of conductive elements, wherein a variation in the GJC implies an abnormal condition;

simulating, via the one or more hardware processors, a plurality of properties of the M-cells, if all the cells in the mid-myocardium are considered to be M-cells, wherein the simulation includes a fivefold decrease in the GJC at an epi-mid mural junction along the whole length of the mid-myocardium, whereas there is no reduction in the GJC at a endo-mid interface;

simulating, via the one or more hardware processor, a plurality of properties of a plurality of M-cell islands, if each M-cell island is considered to be either located completely within the mid-myocardium or partially in a endocardium layer;

recording, via the one or more hardware processors, an effect of physical characteristics of the M-cells on arrhythmogenesis by altering a position, a shape and a size of the M-cells in a plurality of configurations using the simulated M-cells and the plurality of properties of M-cell islands, wherein the each of the plurality of M-cell Islands is modelled as an ellipse positioned vertically with an associated center located in a mid-layer, wherein different sizes of the plurality of M-cell islands are considered in which a minor axis is a constant of ten pixels and a major axis is varied from 25 pixels to 50, 75 and 100 pixels respectively, wherein the position of the plurality of M-cell islands is altered by moving a elliptical island of the major axis 75 pixels and the minor axis 10 pixels to top position and bottom position, and the shape of the plurality of M-cell islands is altered by increasing the minor axis to 15 pixels and the major axis is again varied from 25 pixels to 50, 75 and 100 pixels respectively;

synthesizing, via the one or more hardware processors, a pseudo-ECG by exciting the tissues present in the tissue model, wherein the M-cells present in the tissue model get excited and stimulate neighboring cells by creating a convex wave-front travelling from the endocardium to epicardium and from an apex to a base of the heart; and realizing, via the one or more hardware processors, an effect of short QT syndrome in the tissue model by changing a rectifying potassium current of M-cells to detect cardiac abnormality, wherein the potassium current in epicardial cells is scaled by a pre-defined factor to generate a high, symmetrical T-wave as observed in clinical ECG under short QT syndrome (SQTS) conditions.

13. The one or more non-transitory machine-readable information storage mediums of claim 12 wherein an origin of the array of cells is taken as a bottom leftmost corner.

14. The one or more non-transitory machine-readable information storage mediums of claim 12, wherein the flow of current between two cardiac cells is described using Ohm's law, when there exists a difference in membrane voltage between them.

15. The one or more non-transitory machine-readable information storage mediums of claim 12, wherein two M-cell islands are placed in the mid layer, wherein each of the two M-cell islands is an ellipse with a major axis of 25 pixels and a minor axis of 10 pixels, further wherein each of the two M-cell islands is located at two distinct centers.

16. The one or more non-transitory machine-readable information storage mediums of claim 12, wherein the heart is one of an atlas heart or a personalized heart.

* * * * *